(12) United States Patent
Sugita et al.

(10) Patent No.: US 9,488,568 B2
(45) Date of Patent: Nov. 8, 2016

(54) POLARIZATION ANALYSIS APPARATUS

(71) Applicant: Otsuka Electronics Co., Ltd., Osaka (JP)

(72) Inventors: Kazuhiro Sugita, Hirakata (JP);
Yusuke Yamazaki, Hirakata (JP);
Haruka Otsuka, Hirakata (JP)

(73) Assignee: Otsuka Electronics Co., Ltd., Osaka (JP)

( * ) Notice: Subject to any disclaimer, the term of this patent is extended or adjusted under 35 U.S.C. 154(b) by 27 days.

(21) Appl. No.: 14/568,122

(22) Filed: Dec. 12, 2014

(65) Prior Publication Data

US 2015/0168291 A1 Jun. 18, 2015

(30) Foreign Application Priority Data

Dec. 13, 2013 (JP) ................................. 2013-258095

(51) Int. Cl.
*G01N 21/21* (2006.01)

(52) U.S. Cl.
CPC ....... *G01N 21/211* (2013.01); *G01N 2021/213* (2013.01); *G01N 2201/0675* (2013.01)

(58) Field of Classification Search
CPC ................... G01N 21/211; G01N 2021/213; G01N 2201/0675
See application file for complete search history.

(56) References Cited

U.S. PATENT DOCUMENTS 7,061,613 B1 * 6/2006 Huang .................. G01J 4/04
356/364
2009/0109438 A1 4/2009 Fukue

FOREIGN PATENT DOCUMENTS

| JP | H05-172644 A | 7/1993 |
| JP | 2005-308612 A | 11/2005 |
| JP | 2009-103598 A | 5/2009 |
| JP | 2009-156712 A | 7/2009 |

* cited by examiner

*Primary Examiner* — Kara E Geisel
*Assistant Examiner* — Shawn Decenzo
(74) *Attorney, Agent, or Firm* — Hubbs, Enatsky & Inoue PLLC

(57) ABSTRACT

Provided is a polarization analysis apparatus that can quickly measure the polarization properties of a sample. The polarization analysis apparatus includes a light source configured to emit light in a predetermined wavelength region, a polarizer configured to transmit the light emitted from the light source, a spatial phase modulator configured to transmit the light from the sample, an analyzer configured to transmit the light that has passed through the spatial phase modulator, and an imaging spectrometer configured to receive the light that has passed through the analyzer. The spatial phase modulator is formed of a birefringent material, and is configured to have different phase differences at respective positions in a first direction in a plane orthogonal to an optical axis. The imaging spectrometer disperses the received light in a second direction that is different from the first direction in the plane orthogonal to the optical axis.

5 Claims, 9 Drawing Sheets

POLARIZATION ANALYSIS APPARATUS

INCORPORATION BY REFERENCE

The present disclosure contains subject matter related to that disclosed in Japanese Priority Patent Application JP2013-258095 filed in the Japan Patent Office on Dec. 13, 2013, the entire contents of which are hereby incorporated by reference.

BACKGROUND OF THE INVENTION

1. Field of the Invention

The present application relates to a polarization analysis apparatus.

2. Description of the Related Art

Japanese Patent Application Laid-open No. 2009-103598 discloses a spectroscopic ellipsometer configured to acquire a polarization state of a sample based on a rotating analyzer method.

Japanese Patent Application Laid-open No. Hei 5-172644 discloses a Stokes meter configured to determine the sign of the Stokes parameter S2 based on a phase modulation method using a photoelastic modulator.

However, with the spectroscopic ellipsometer disclosed in Japanese Patent Application Laid-open No. 2009-103598, light needs to be detected at each angle by mechanically rotating the analyzer, and hence the measurement takes time. Further, with the Stokes meter disclosed in Japanese Patent Application Laid-open No. Hei 5-172644, when spectrometry is performed, the light needs to be detected at each stage by varying the applied voltage of the photoelastic modulator at each measurement wavelength, and hence the measurement takes time.

It is an object of the present invention, which has been made in view of the above-mentioned problems, to provide a polarization analysis apparatus that can quickly measure the polarization properties of a sample.

SUMMARY OF THE INVENTION

In order to achieve the above-mentioned object, according to one embodiment of the present invention, there is provided a polarization analysis apparatus, including: a light source configured to emit light in a predetermined wavelength region; a polarizer configured to transmit the light emitted from the light source, the light having passed through the polarizer being radiated on a sample; a spatial phase modulator configured to transmit the light from the sample, the spatial phase modulator being formed of a birefringent material and being configured to have different phase differences at respective positions in a first direction in a plane orthogonal to an optical axis; an analyzer configured to transmit the light that has passed through the spatial phase modulator; and an imaging spectrometer configured to receive the light that has passed through the analyzer, and disperse the received light in a second direction that is different from the first direction in the plane orthogonal to the optical axis.

DETAILED DESCRIPTION OF THE INVENTION

An embodiment of the present invention is described below with reference to the drawings.

[First Example of Polarization Analysis Apparatus]

Figure 1:
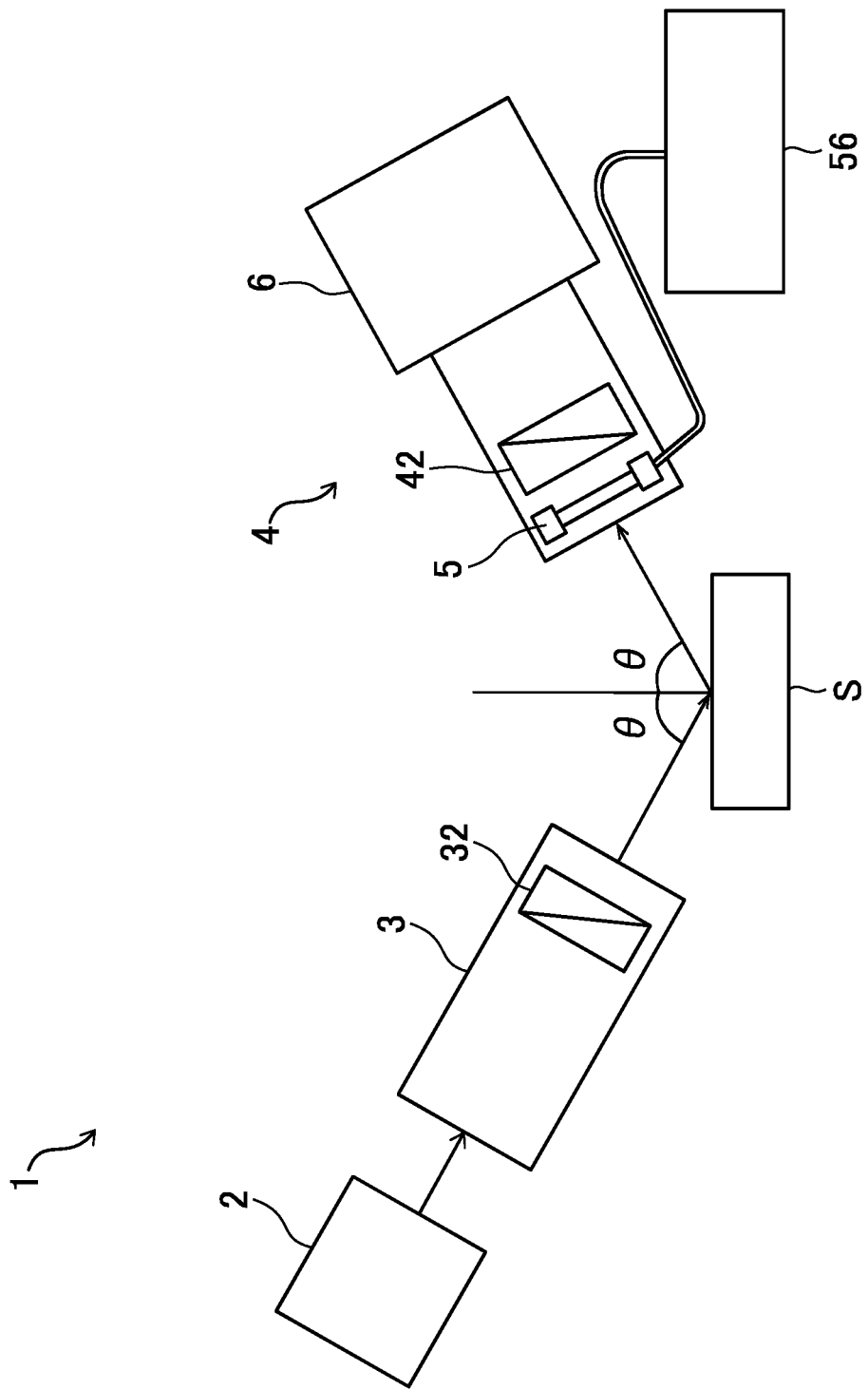
FIG. 1 is a diagram illustrating an outline of a first example of a polarization analysis apparatus.

FIG. 1 is a diagram illustrating an outline of a polarization analysis apparatus 1 according to a first example. The polarization analysis apparatus 1 according to the first example is a spectroscopic ellipsometer.

The polarization analysis apparatus 1 includes a light source 2 that generates light to be radiated on a sample S, a projection unit 3 that irradiates the sample S with the light generated by the light source 2, and a light receiving unit 4 that receives the light reflected by the sample S.

It is preferred that the light source 2 be a white light source that has a flat output characteristic over a wide wavelength region. For example, a deuterium lamp or a tungsten lamp may be employed for the light source 2. It is preferred that the light emitted by the light source 2 has a wavelength region that is at least, for example, 100 nm wide, more preferably, 200 nm wide. The wavelength region may be arbitrarily defined within a region including the near-ultraviolet region (about 200 to 400 nm), the visible region (about 400 to 800 nm), and the near-infrared region (about 800 to 1,000 nm). For example, the wavelength region may include all of the visible region, may straddle the near-ultraviolet region and the visible region, or may even straddle the visible region and the near-infrared region.

The projection unit 3 is supported movably in a circumferential direction about the sample S in a manner that allows the incident angle of light to be changed. The projection unit 3 includes a polarizer 32. Light that passes through the polarizer 32 is polarized into linearly-polarized light.

The light receiving unit 4 is supported movably in a circumferential direction about the sample S in a manner that allows the detection angle of light to be changed. The light receiving unit 4 includes a spatial phase modulator 5, an analyzer 42, and an imaging spectrometer 6.

Figure 2:
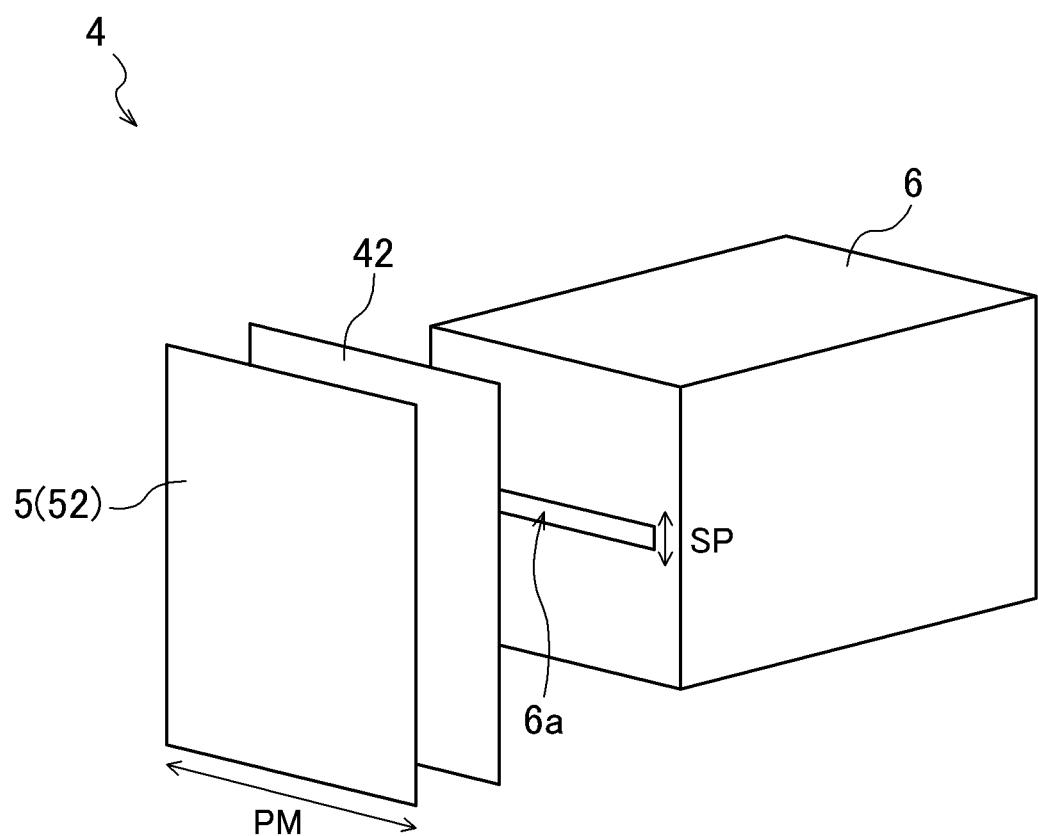
FIG. 2 is a diagram illustrating an outline of an example of a light receiving unit.

FIG. 2 is a diagram illustrating an outline of an example of the light receiving unit 4. In the light receiving unit 4, the spatial phase modulator 5, the analyzer 42, and the imaging spectrometer 6 are arranged in a line in this order from an upstream direction to a downstream direction of the light.

The spatial phase modulator 5, which is formed of a birefringent material, is configured to have different phase differences at respective positions in a phase modulation direction PM in a plane orthogonal to the optical axis. The phase modulation direction PM corresponds to the longitudinal direction of a slit 6a of the imaging spectrometer 6. The spatial phase modulator 5 transmits light in a predetermined wavelength region, namely, white light, generated by the light source 2. The directions of the fast axis and the slow axis of the spatial phase modulator 5 are not especially limited. For example, the fast axis may be set to be parallel to the phase modulation direction PM, and the slow axis may be set to be perpendicular to the phase modulation direction PM. The spatial phase modulator 5 is described in more detail below.

Light that has passed through the spatial phase modulator 5 passes through the analyzer 42, and then arrives at the imaging spectrometer 6. It is preferred that the angle difference between the direction of each of the fast axis and the slow axis of the spatial phase modulator 5 and the polarization direction of the analyzer 42 be, for example, 45°. It is preferred that the angle difference between the polarization direction of the polarizer 32 and the polarization direction of the analyzer 42 be, for example, 0°.

The imaging spectrometer 6 includes a grating (a diffraction grating) that disperses the light coming from the slit 6a, and an image sensor formed from imaging elements, such as CCDs, that are arrayed in two dimensions. The light that has passed through the analyzer 42 is formed into a line shape by the slit 6a, and enters the imaging spectrometer 6. The grating disperses the light coming from the slit 6a in a spectral direction SP in a plane orthogonal to the optical axis. The spectral direction SP, which corresponds to the width direction of the slit 6a, is orthogonal to the phase modulation direction PM. The image sensor receives light having different phase differences at respective positions in the phase modulation direction PM and different wavelengths at respective positions in the spectral direction SP. Consequently, spectral information corresponding to phase difference can be acquired in one shot.

An arithmetic device (not shown) calculates a phase difference Δ, an amplitude ratio angle Ψ, and the like at each wavelength by data analysis based on the spectral information corresponding to phase difference acquired by the imaging spectrometer 6, and ultimately calculates a film thickness, an optical constant, and the like.

Figure 3:
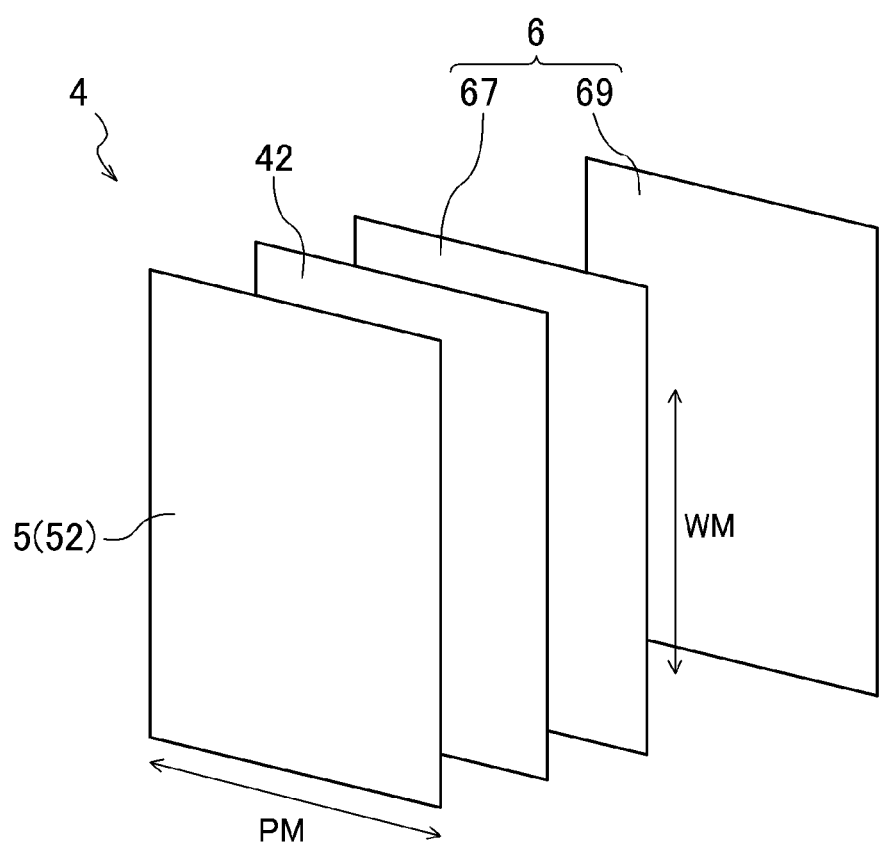
FIG. 3 is a diagram illustrating an outline of a modified example of the light receiving unit.

As illustrated in FIG. 3, for example, the imaging spectrometer 6 may include a tunable filter 67 and an image sensor 69. The tunable filter 67 modulates the wavelength of the light passing through the tunable filter 67 so that the light has different wavelengths at respective positions in a wavelength modulation direction WM in a plane orthogonal to the optical axis. The wavelength modulation direction WM is orthogonal to the phase modulation direction PM.

Figure 4:
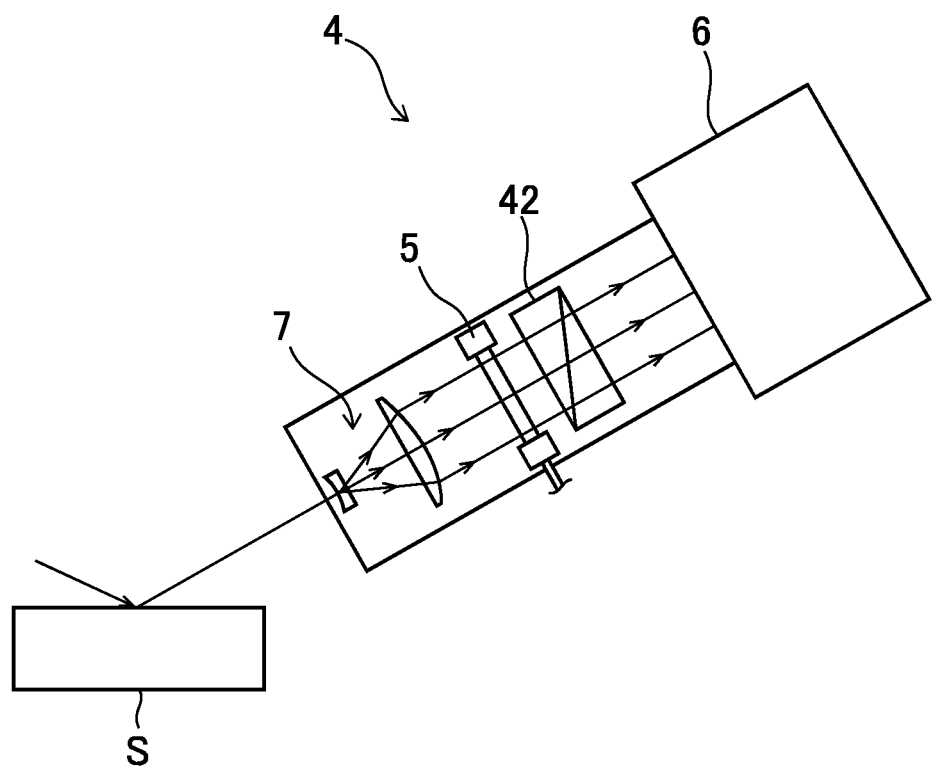
FIG. 4 is a diagram illustrating an outline of another modified example of the light receiving unit.

As illustrated in FIG. 4, for example, the light receiving unit 4 may further include a beam expander 7. The beam expander 7 expands the diameter of the beam of light reflected by the sample S, and irradiates the spatial phase modulator 5 with the expanded light beam. It is preferred to include such a beam expander 7 when the spot diameter of the light radiated on the sample S from the projection unit 3 is small.

Figure 5:
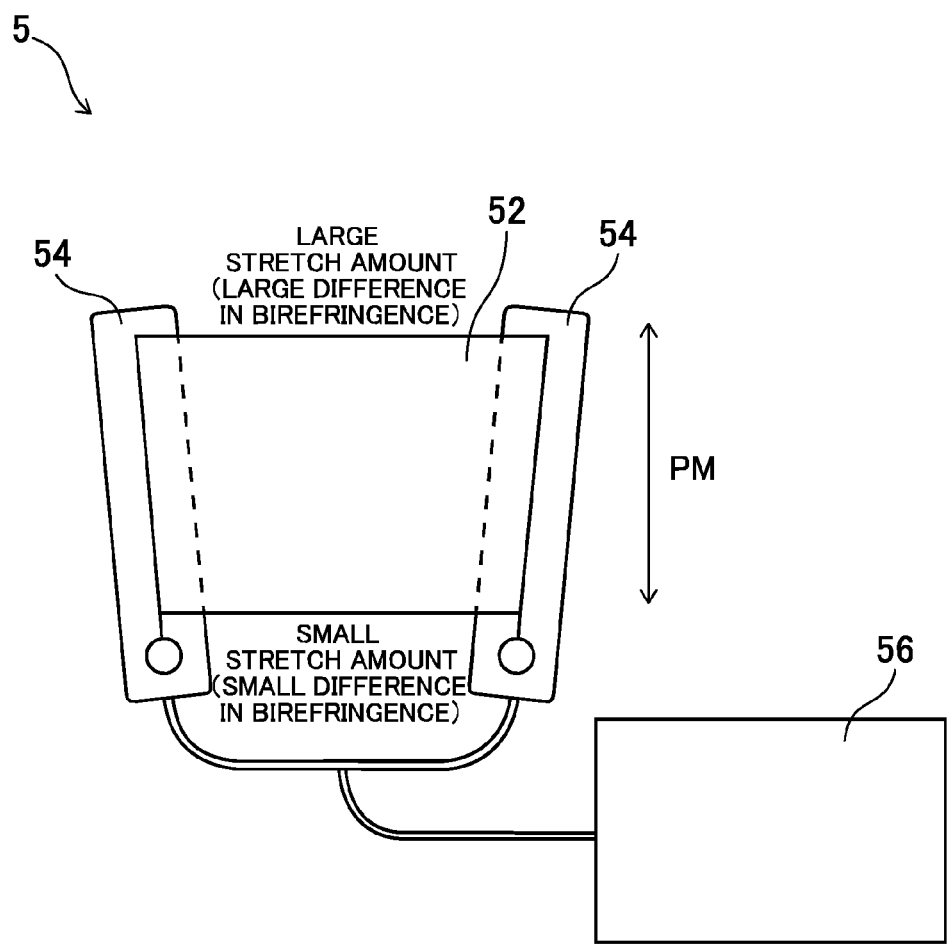
FIG. 5 is a diagram illustrating an outline of an example of a spatial phase modulator.

FIG. 5 is a diagram illustrating an outline of an example of the spatial phase modulator 5. The spatial phase modulator 5 includes a phase difference film 52 formed of a birefringent material, a pair of stretching devices 54 arranged on both sides of the phase difference film 52, and a controller 56 connected to the pair of stretching devices 54.

The pair of stretching devices 54 stretch the phase difference film 52 in the shape of a fan having a comparatively smaller stretch amount on one side in the width direction (the vertical direction in FIG. 5) of the phase difference film 52, and a comparatively larger stretch amount on the other side. At this time, the difference in birefringence of the phase difference film 52 is comparatively small on one side in the width direction, and comparatively large on the other. The difference in birefringence continuously increases from one side to the other in the width direction. In conjunction with this, the phase difference of the phase difference film 52 also continuously increases from one side to the other in the width direction. Namely, the width direction of the phase difference film 52 serves as the phase modulation direction PM. It is preferred that the phase difference film 52 include a range in which the phase difference in the phase modulation direction PM changes from 0 to 1 wavelength (360°).

The controller 56 adjusts the stretch amount of the phase difference film 52 to compensate for the temperature dependency of the properties of the phase difference film 52. Further, the controller 56 may also adjust the temperature of the phase difference film 52 to compensate for the temperature dependency of the properties of the phase difference film 52.

Note that, the spatial phase modulator 5 is not limited to the above-mentioned mode. The spatial phase modulator 5 can be an optical component and the like configured so that the phase difference changes in the above manner in one direction.

[Second Example of Polarization Analysis Apparatus]

Figure 6:
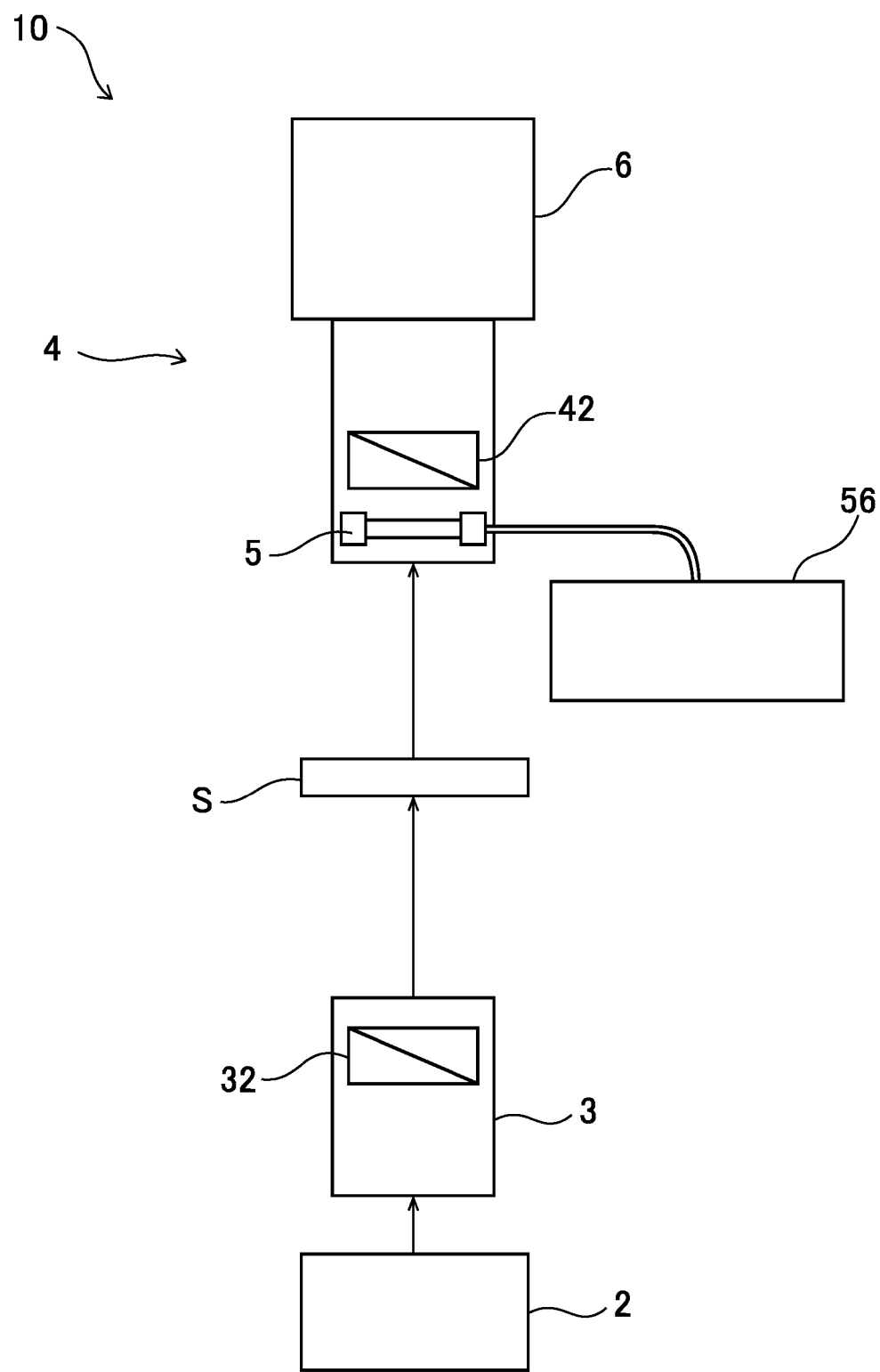
FIG. 6 is a diagram illustrating an outline of a second example of the polarization analysis apparatus.

FIG. 6 is a diagram illustrating an outline of a polarization analysis apparatus 10 according to a second example. Structures in the polarization analysis apparatus 10 that are the same as those in the above-mentioned first example are denoted with the same reference numeral, and a detailed description thereof is omitted here. In this second example, the projection unit 3 and the light receiving unit 4 are arranged opposing each other, and the light receiving unit 4 receives light that has passed through the sample S.

[Modified Example of Light Receiving Unit]

Figure 7:
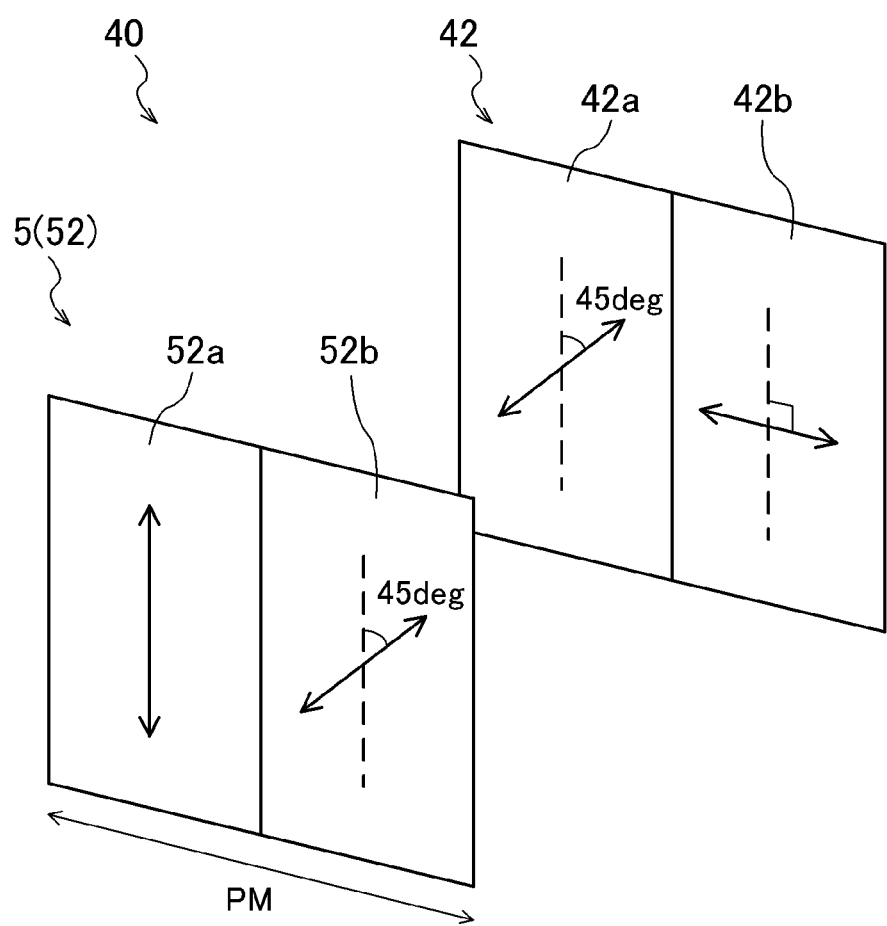
FIG. 7 is a diagram illustrating an outline of a modified example of the light receiving unit.

FIG. 7 is a diagram illustrating an outline of a light receiving unit 40 according to a modified example. FIG. 7 illustrates only the spatial phase modulator 5 and the analyzer 42 included in the light receiving unit 40, and the imaging spectrometer 6 is not shown. This modified example can even be applied to the first example or to the second example.

In this modified example, the spatial phase modulator 5 includes two regions 52a and 52b that are adjacent in the phase modulation direction PM. The direction of each of the fast axis and the slow axis of the first region 52a and the direction of each of the fast axis and the slow axis of the second region 52b are different from each other. It is preferred that the angle difference between the two directions be, for example, 45°. Both the arrows illustrated inside the two regions 52a and 52b in FIG. 7 represent the direction of the fast axis.

Similarly, the analyzer 42 also includes two regions 42a and 42b that are adjacent in the phase modulation direction PM. The polarization direction of the first region 42a and the polarization direction of the second region 42b are different from each other. It is preferred that the angle difference between the two directions be, for example, 45°. Both the arrows illustrated inside the two regions 42a and 42b in FIG. 7 represent the polarization direction.

The first region 52a of the spatial phase modulator 5 and the first region 42a of the analyzer 42 oppose each other. Light that has passed through the first region 52a of the spatial phase modulator 5 passes through the first region 42a of the analyzer 42, and then arrives at the imaging spectrometer 6. It is preferred that the angle difference between the direction of each of the fast axis and the slow axis of the first region 52a of the spatial phase modulator 5 and the polarization direction of the first region 42a of the analyzer 42 be, for example, 45°.

The second region 52b of the spatial phase modulator 5 and the second region 42b of the analyzer 42 oppose each other. Light that has passed through the second region 52b of the spatial phase modulator 5 passes through the second region 42b of the analyzer 42, and then arrives at the imaging spectrometer 6. It is preferred that the angle difference between the direction of each of the fast axis and the slow axis of the second region 52b of the spatial phase modulator 5 and the polarization direction of the second region 42b of the analyzer 42 be, for example, 45°.

It is preferred that the two regions 52a and 52b of the spatial phase modulator 5 each include a range in which the phase difference in the phase modulation direction PM changes from 0 to 1 wavelength) (360°. Such two regions 52a and 52b may be realized by, for example, providing two sets of the phase difference film 52, the pair of stretching devices 54, and the controller 56 illustrated in FIG. 5 described above.

When the light receiving unit 40 according to the thus-described modified example is used, all of Stokes parameters S1, S2, and S3 can be calculated. A case is now described below in which the light receiving unit 40 according to the modified example is applied to each of the above-mentioned first example and second example.

Note that, in the following description, the angle of the polarization direction of the polarizer 32 is expressed based on the fast axis of the first region 52a of the spatial phase modulator 5 (refer to FIG. 7).

[Application to First Example]

Figure 8:
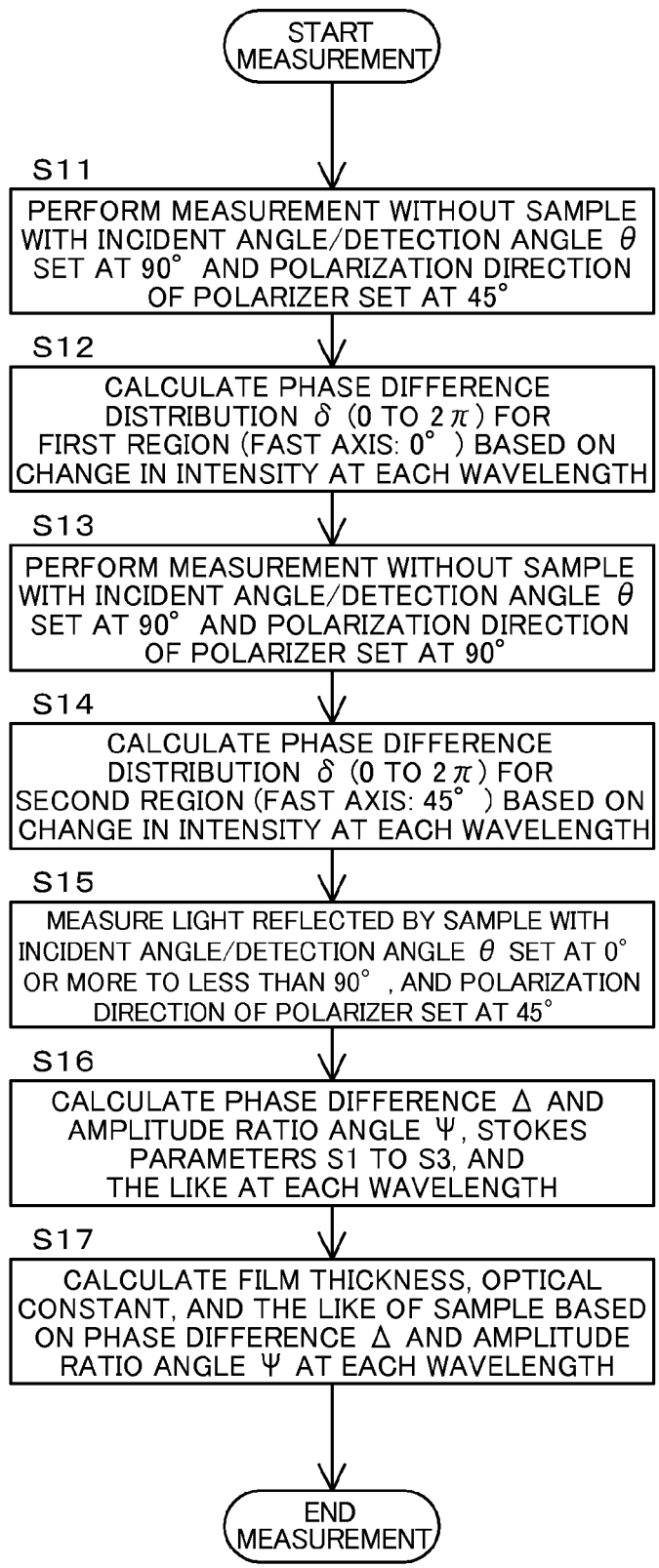
FIG. 8 is a flowchart illustrating application to the first example.

FIG. 8 is a flowchart illustrating measurement when the light receiving unit 40 according to the modified example is applied in the polarization analysis apparatus 1 according to the first example (refer to FIG. 1).

In Step S11, measurement is carried out without the sample S, with the incident angle/detection angle θ set at 90°, and the polarization direction of the polarizer 32 set at 45°. Namely, by setting the incident angle/detection angle θ to 90°, the projection unit 3 and the light receiving unit 4 are made to oppose each other, and the intensity of light that has passed through only the air between the projection unit 3 and the light receiving unit 4 is measured by the imaging spectrometer 6.

In Step S12, a phase difference distribution δ (0 to 2π) of the first region 52a (fast axis: 0°) of the spatial phase modulator 5 is calculated using the equation (2) described below based on the change in intensity at each wavelength measured by the imaging spectrometer 6.

In Step S13, measurement is carried out without the sample S, with the incident angle/detection angle θ set at 90°, and the polarization direction of the polarizer 32 set at 90°. Namely, by setting the incident angle/detection angle θ to 90°, the projection unit 3 and the light receiving unit 4 are made to oppose each other, and the intensity of light that has passed through only the air between the projection unit 3 and the light receiving unit 4 is measured by the imaging spectrometer 6.

In Step S14, a phase difference distribution δ (0 to 2π) of the second region 52b (fast axis: 45°) of the spatial phase modulator 5 is calculated using the equation (2) described below based on the change in intensity at each wavelength measured by the imaging spectrometer 6.

In Step S15, the intensity of light reflected by the sample S is measured by the imaging spectrometer 6 with the incident angle/detection angle θ set at 0° or more to less than 90°, and the polarization direction of the polarizer 32 set at 45°.

In Step S16, the phase difference Δ, the amplitude ratio angle Ψ, the Stokes parameters S1, S2, and S3, and the like at each wavelength are calculated based on the equations (3), (4), and (5) described below.

In Step S17, the film thickness, the optical constant, and the like of the sample S are calculated based on the phase difference Δ, the amplitude ratio angle Ψ, and the like at each wavelength.

[Application to Second Example]

Figure 9:
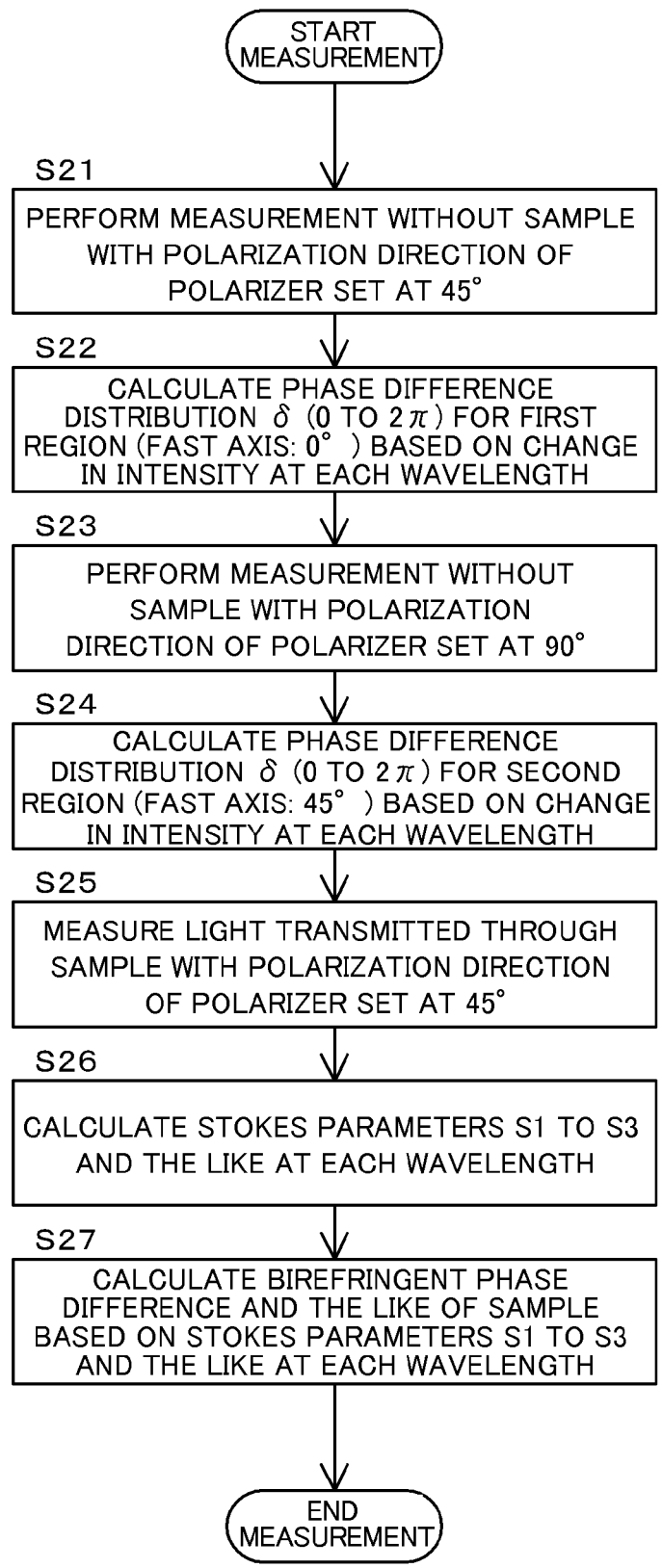
FIG. 9 is a flowchart illustrating application to the second example.

FIG. 9 is a flowchart illustrating measurement when the light receiving unit 40 according to the modified example is applied in the polarization analysis apparatus 10 according to the second example (refer to FIG. 6).

In Step S21, measurement is carried out without the sample S, with the polarization direction of the polarizer 32 set at 45°. Namely, the intensity of light that has passed through only the air between the projection unit 3 and the light receiving unit 4 is measured by the imaging spectrometer 6.

In Step S22, a phase difference distribution δ (0 to 2π) of the first region 52a (fast axis: 0°) of the spatial phase modulator 5 is calculated using the equation (2) described below based on the change in intensity at each wavelength measured by the imaging spectrometer 6.

In Step S23, measurement is carried out without the sample S, with the polarization direction of the polarizer 32 set at 90°. Namely, the intensity of light that has passed through only the air between the projection unit 3 and the light receiving unit 4 is measured by the imaging spectrometer 6.

In Step S24, a phase difference distribution δ (0 to 2π) of the second region 52b (fast axis: 45°) of the spatial phase modulator 5 is calculated using the equation (2) described below based on the change in intensity at each wavelength measured by the imaging spectrometer 6.

In Step S25, the intensity of light that has passed through the sample S is measured by the imaging spectrometer 6 with the polarization direction of the polarizer 32 set at 45°.

In Step S26, the Stokes parameters S1, S2, and S3, and the like at each wavelength are calculated based on the equations (3), (4), and (5) described below.

In Step S27, the birefringent phase difference and the like of the sample S are calculated based on the Stokes parameters S1 to S3 and the like at each wavelength.

[Derivation of Stokes Parameters]

Derivation of the Stokes parameters S1 to S3 is described with reference to equations.

Light intensity I(δ) of δ=0 to 2π measured by the imaging spectrometer 6 when the polarization direction of the polarizer is set to 32 to 45°, and the angle difference between the direction of each of the fast axis and the slow axis of the spatial phase modulator 5 and the polarization direction of the analyzer is set to 42 to 45° can be expressed by the following equation (1). The symbol δ represents the phase difference of the spatial phase modulator 5.

$$I(\delta)=I_0[1+\sin 2\Psi \sin \Delta \sin \delta+(\cos 2\Psi \sin 2M+\sin 2\Psi \cos \Delta \cos 2M)\cos \delta]=I_0[1-S_3 \sin \delta+(-S_1 \sin 2M+S_2 \cos 2M)\cos \delta] \quad (1)$$

When there is no sample S, the following equation (2) can be obtained by simplifying the above-mentioned equation (1).

$$I(\delta)=I_0[1+\cos \delta] \quad (2)$$

The light intensity I(δ) of δ=0 to 2π measured by the imaging spectrometer 6 when the polarization direction of the polarizer 32 is set to 90°, and the angle difference between the direction of each of the fast axis and the slow axis of the spatial phase modulator 5 and the polarization direction of the analyzer 42 is set to 45°, can also be expressed by the above-mentioned equation (1), and the above-mentioned equation (2) is obtained when there is no sample S.

A phase difference distribution is determined from the above-mentioned equation (2), and used in the following equations (3) and (4). The phase difference Δ and the amplitude ratio angle Ψ of the sample S are obtained from these equations (3) and (4).

Regarding the first region 52a (fast axis: 0°) of the spatial phase modulator 5, the above-mentioned equation (1) turns into the following equation (3), and hence the phase difference Δ and the amplitude ratio angle Ψ of the sample S are obtained by solving the equation (3) by a least-squares method, for example, by utilizing the light intensity measured for a plurality of values of δ.

$$I(\delta) = I_0[1 + \sin 2\Psi \sin \Delta \sin \delta + \sin 2\Psi \cos \Delta \cos \delta] \quad (3)$$

Regarding the second region 52b (fast axis: 45°) of the spatial phase modulator 5, the above-mentioned equation (1) turns into the following equation (4), and hence the phase difference Δ and the amplitude ratio angle Ψ of the sample S are obtained by solving the equation (4) by a least-squares method, for example, by utilizing the light intensity measured for a plurality of values of δ.

$$I(\delta) = I_0[1 + \sin 2\Psi \sin \Delta \sin \delta + \cos 2\Psi \cos \delta] \quad (4)$$

The Stokes parameters S1, S2, and S3 are obtained from the following equation (5) utilizing the phase difference Δ and the amplitude ratio angle Ψ of the sample S.

$$S_1 = -\cos 2\Psi, \ S_2 = \sin 2\Psi \cos \Delta, \ S_3 = -\sin 2\Psi \sin \Delta \quad (5)$$

When the phase difference Δ and the amplitude ratio angle Ψ of the sample S are obtained, because the light intensity measured at each wavelength and each phase is utilized, the phase difference Δ and the amplitude ratio angle Ψ of a plurality of wavelengths can be obtained in one go. Consequently, measurement accuracy can be improved.

In the related-art rotating analyzer method or phase modulation method, there is a limit to the number of Stokes parameters that can be calculated. However, according to the method described above, all of the Stokes parameters S1, S2, and S3 can be calculated.

An embodiment of the present invention has been described above. However, the present invention is not limited to the above-mentioned embodiment, and obviously various modifications could be carried out by the person skilled in the art.

What is claimed is:

1. A polarization analysis apparatus, comprising:
   a light source configured to emit light in a predetermined wavelength region;
   a polarizer configured to transmit the light emitted from the light source, the light having passed through the polarizer being radiated on a sample;
   a spatial phase modulator configured to transmit the light from the sample, the spatial phase modulator being formed of a birefringent material and being configured to have different phase differences at respective positions in a first direction in a plane orthogonal to an optical axis;
   an analyzer configured to transmit the light that has passed through the spatial phase modulator;
   an imaging spectrometer configured to receive the light that has passed through the analyzer, and disperse the received light in a second direction that is different from the first direction in the plane orthogonal to the optical axis, and
   wherein the spatial phase modulator comprises two regions that are adjacent in the first direction, the two regions having different directions in one of a fast axis and a slow axis.

2. The polarization analysis apparatus according to claim 1, wherein a phase difference of the spatial phase modulator continuously changes in the first direction.

3. The polarization analysis apparatus according to claim 1, wherein a difference in birefringence of the spatial phase modulator continuously changes in the first direction.

4. The polarization analysis apparatus according to claim 1, further comprising a beam expander configured to expand a diameter of a beam of the light from the sample, and irradiate the spatial phase modulator with the expanded light beam.

5. The polarization analysis apparatus according to claim 1, wherein the analyzer comprises two regions that are adjacent in the first direction, the two regions respectively corresponding to the two regions of the spatial phase modulator, and having different polarization directions from each other.

* * * * *